United States Patent
Masek et al.

(10) Patent No.: US 9,797,820 B2
(45) Date of Patent: Oct. 24, 2017

(54) LOADCELL PROBE FOR OVERLOAD PROTECTION

(71) Applicant: ILLINOIS TOOL WORKS INC., Glenview, IL (US)

(72) Inventors: William Masek, North Atleboro, MA (US); Peter Bermudez, Dartmouth, MA (US); Stephen M. McMahon, Quincy, MA (US); Adrian Riddick, Medfield, MA (US); Fernando L. Castro, Westwood, MA (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 15/033,234

(22) PCT Filed: Nov. 4, 2014

(86) PCT No.: PCT/US2014/063844
§ 371 (c)(1),
(2) Date: Apr. 29, 2016

(87) PCT Pub. No.: WO2015/069633
PCT Pub. Date: May 14, 2015

(65) Prior Publication Data
US 2016/0252437 A1 Sep. 1, 2016

Related U.S. Application Data

(60) Provisional application No. 61/900,778, filed on Nov. 6, 2013.

(51) Int. Cl.
*G01N 3/00* (2006.01)
*G01N 3/08* (2006.01)
(Continued)

(52) U.S. Cl.
CPC ............... *G01N 3/08* (2013.01); *G01N 3/02* (2013.01); *G01L 1/04* (2013.01); *G01L 5/108* (2013.01);
(Continued)

(58) Field of Classification Search
CPC ... G01N 2203/0204; G01N 2203/0012; G01N 3/42; G01N 3/08; G01N 3/02; G01L 1/04; G01L 5/108
(Continued)

(56) References Cited

U.S. PATENT DOCUMENTS 1,192,670 A * 7/1916 Moore et al. ............ G01N 3/42
73/81
1,381,288 A * 6/1921 Davis ....................... G01N 3/42
73/81
(Continued)

FOREIGN PATENT DOCUMENTS

CN 101042322 A 9/2007
DE 4112371 A1 10/1992
(Continued)

OTHER PUBLICATIONS

ISR and WO for PCT/US2014/063844 dated Jan. 27, 2015.

*Primary Examiner* — Jonathan Dunlap
(74) *Attorney, Agent, or Firm* — McCarter & English, LLP

(57) ABSTRACT

The present disclosure provides an electro-mechanical fuse-type configuration built into the probe that contacts the specimen during materials testing. The design includes an internal pre-loaded compression spring and an electrical contact switch. The coil spring preloaded to the desired safety load results in the probe assembly directly passing the load from the probe tip to the load cell for loads under the point where the spring additionally compresses. Upon
(Continued)

deflection of the spring in excess of safety preload, the spring internally compresses within the probe coupling rather than the probe tip continuing to displace into the specimen, thereby switching the state of the electrical contact switch and stopping operation of the materials testing device. In a further configuration, excessive travel of the load cell coupling is detected, and, in response, operation of the materials testing device is stopped.

14 Claims, 4 Drawing Sheets

(51) Int. Cl.
*G01N 3/02* (2006.01)
*G01L 5/10* (2006.01)
*G01N 3/42* (2006.01)
*G01L 1/04* (2006.01)

(52) U.S. Cl.
CPC ....... *G01N 3/42* (2013.01); *G01N 2203/0012* (2013.01); *G01N 2203/0204* (2013.01)

(58) Field of Classification Search
USPC ................................ 73/81, 862.621, 818, 85
See application file for complete search history.

(56) References Cited

U.S. PATENT DOCUMENTS

| | | | |
|---|---|---|---|
| 1,768,512 A * | 6/1930 | De Leeuw | G01N 3/42 346/150.2 |
| 2,388,256 A * | 11/1945 | Davis, Jr. | G01P 3/50 73/769 |
| 2,833,141 A * | 5/1958 | Holm | G01M 3/3281 73/40 |
| 3,786,676 A | 1/1974 | Korolyshun et al. | |
| 3,934,463 A * | 1/1976 | Venderjagt | G01N 3/42 73/81 |
| 4,262,525 A | 4/1981 | Ernst | |
| 5,092,175 A * | 3/1992 | Winckler | G01N 3/405 73/573 |
| 5,319,979 A * | 6/1994 | Abrahamson | G01L 9/006 73/723 |
| 5,696,312 A * | 12/1997 | Lee | G01N 3/48 73/12.02 |
| 5,739,411 A * | 4/1998 | Lee | G01N 3/48 73/12.09 |
| 5,879,312 A * | 3/1999 | Imoto | A61B 5/0053 600/587 |
| 8,156,802 B2 * | 4/2012 | Werber | G01L 1/26 73/159 |
| 8,646,328 B2 * | 2/2014 | Knowles | G01F 23/2961 73/290 V |
| 8,850,901 B2 * | 10/2014 | Mankame | F03G 7/065 73/862.381 |
| 9,546,939 B2 * | 1/2017 | Liu | G01N 3/08 |
| 2004/0134285 A1 | 7/2004 | Koniger et al. | |
| 2008/0184807 A1 * | 8/2008 | Nakano | G01N 3/08 73/818 |
| 2010/0024543 A1 * | 2/2010 | Knowles | G01F 23/2961 73/290 V |
| 2014/0216169 A1 * | 8/2014 | Romo | G01L 5/0057 73/862.01 |
| 2015/0075295 A1 * | 3/2015 | Romo | B66B 7/025 73/862.01 |
| 2015/0323436 A1 * | 11/2015 | Hansma | A61B 5/0053 73/12.09 |

FOREIGN PATENT DOCUMENTS

| | | |
|---|---|---|
| DE | 9319668 U1 | 4/1995 |
| DE | 102010026894 A1 | 1/2012 |
| EP | 0012728 A1 | 6/1980 |
| JP | S5794626 A | 6/1982 |
| JP | H1123434 A | 1/1999 |

* cited by examiner

LOADCELL PROBE FOR OVERLOAD PROTECTION

This application is a National Phase of International Application No. PCT/US2014/063844, filed Nov. 4, 2014, and claims priority of U.S. Provisional Application Ser. No. 61/900,778, filed on Nov. 6, 2013, the contents of which is hereby incorporated by reference herein in its entirety.

BACKGROUND OF THE DISCLOSURE

Field of the Disclosure

The present disclosure relates to an overload protection for a loadcell probe so that a specimen or device under test is protected when excessive forces are applied by the probe during materials testing.

Description of the Prior Art

Materials testing machines used to measure force and displacement of compliant surfaces under compression use a loadcell force sensor with a probe to contact the specimen under test. The probe is driven into the specimen with a precision linear drive system and the displacement is measured with a linear or rotary position encoder. The materials testing machine has software designed to command and control the position of the probe with force feedback provided by the loadcell via the probe contacting the compliant specimen. There are some applications, typically in automated environments such as assembly lines in factories, whereby the load testing machine is connected to external software that initiates motion commands to start and stop tests as well as to collect and process the materials testing machine's test results.

There can be occasions where the control of the drive axis can become abnormal and unpredictable. One example of abnormal behavior of the system is where the drive system that positions the probe into the specimen unintentionally drives "open loop" at high rate of speed introducing a very high load into the specimen. This scenario can damage the specimen under test or nearby equipment and/or represents a safety risk to people around the test equipment. There are typically several software and electronic speed and load limits in place on the materials testing machine that are expected to stop this inadvertent out of control motion. In some cases, however, the out of control condition can either occur too quickly or during a state of non-communication or "hanging up" condition by the control software whereby the software or electrical limits cannot react in time and the crash event cannot be prevented through the normal means.

Some possible causes of the drive system's motion to become unpredictable and lose control could be:
Failure in a drive system hardware component (motor, encoder, power amplifier, cables)
Software bugs
Incompatible interaction between the testing machine's software, hardware and firmware
Interaction with the factory's software that commands and controls the load test machine
Environmental conditions—operators, power spikes or surges.

A common method to limit the torque to a motor is to use an electrical or mechanical friction slip clutch in between the motor and drive shaft. This approach was not satisfactory for this design because it is not at the point of application of the load/specimen and because the system draws high currents during its normal operation—particularly when the drive system needs to accelerate and decelerate. Additionally, a friction clutch could slip under these conditions, which would be undesirable.

SUMMARY OF THE DISCLOSURE

The present disclosure provides an electro-mechanical fuse-type configuration built into the probe that contacts the specimen in materials testing. The disclosed design includes a two-piece probe coupling with an internal pre-loaded compression spring and an electrical contact switch. The spring preloaded to the desired safety load results in the probe assembly directly passing the load from the probe tip to the load cell for loads under the point where the spring additionally compresses. Upon deflection of the spring in excess of safety preload, the spring internally compresses within the probe coupling rather than the probe tip continuing to displace into the specimen. The compression of the spring continues upon additional displacement by the drive system until an electrical contact is broken. The electrical contact is wired to the material testing machine's emergency stop and when it is broken the emergency stop is tripped and instantly shuts down the material testing machine preventing any further motion of the probe and damage to the specimen. This is shown schematically in FIG. 1 which shows the probe in its normal state applying light loads to the specimen. FIG. 2 shows the probe coupling and spring undergoing compression beyond the safe preload and displacement limit, thereby breaking the electrical contact and tripping the emergency stop to stop the materials testing machine.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENTS

Figure 1:
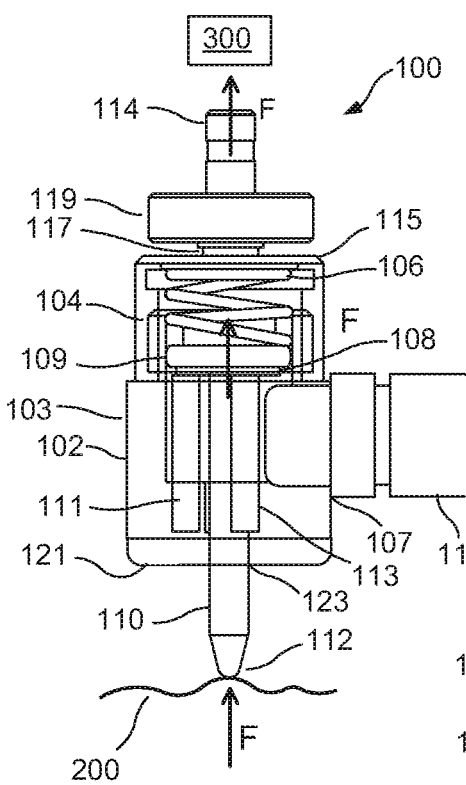
FIG. 1 is a cross-sectional view of a first embodiment of the probe assembly of the present disclosure, in a normal state.
Figure 2:
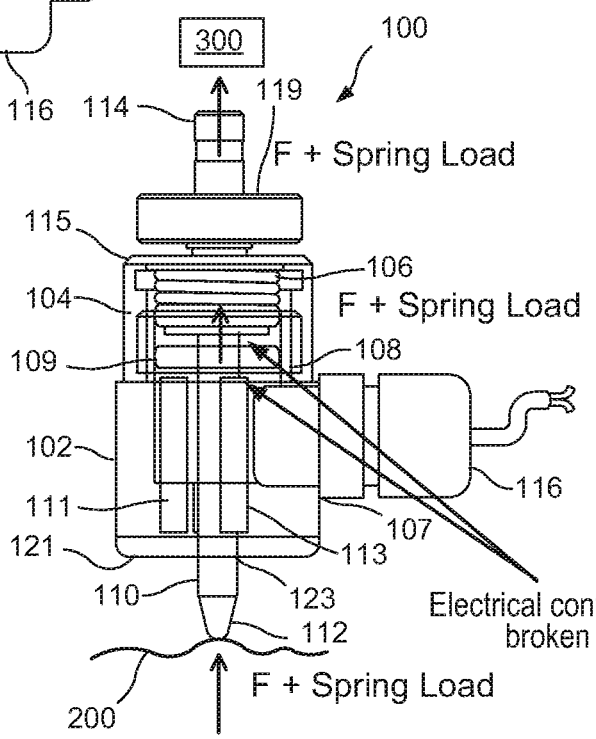
FIG. 2 is a cross-sectional view of a first embodiment of the probe assembly of the present disclosure, in a safety or compressed state.
Figure 3:
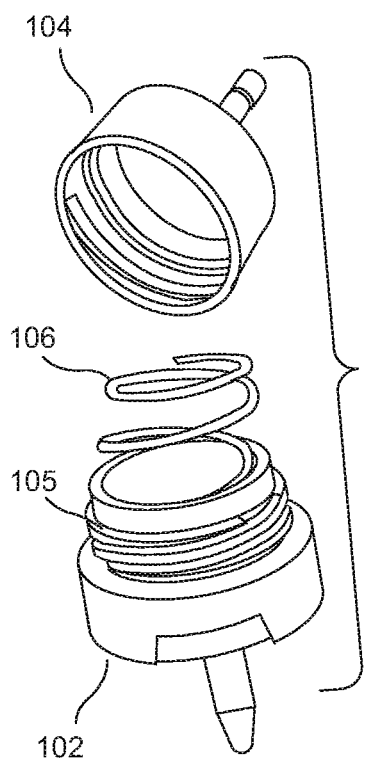
FIG. 3 is a perspective view of the disassembled probe assembly of the first embodiment of the present disclosure.

Referring now to the drawings in detail wherein like numerals refer to like elements throughout the several views, one sees that FIGS. 1-6 disclose a first embodiment the probe assembly 100 (or probe coupling) of the present disclosure in the normal state (FIG. 1), the safety state (FIG. 2) and the disassembled state (FIG. 3). FIGS. 1-3 illustrate that the probe assembly 100 includes a lower casing 102 and an upper casing 104 with an internal pre-loaded compression spring 106 and an electrical contact switch 108. The probe 110 includes a lower probe tip 112 which contacts the specimen or test surface 200.

As shown in FIG. 1, the probe assembly 100 includes a cylindrical lower casing 102 which is hollow and typically made from stainless steel or a similar metal. The lower casing 102 includes an outer cylindrical wall 103 which is integral with an upper inner support wall 105, including an external threaded surface, configured for threaded engagement with internal threaded surface in the upper casing 104 whereby upper casing 104 is positioned concentrically outwardly adjacent from the upper inner support wall 105 in a threaded engagement. The lower casing 102 and the upper casing 104 share a common longitudinal axis. The cylindrical upper casing 104 threadedly engages over the upper inner support wall 105 of the lower casing 102. Outer cylindrical wall 103 of lower casing 102 further includes lateral aperture 107 through which plug 116 extends, wherein the longitudinal or rotational axis of cylindrical plug 116 is perpendicular to the longitudinal or rotational axis of the cylindrical lower casing 102. Plug 116 is configured and arranged to be electrically wired to the emergency stop of the associated materials testing machine 300, so that the materials testing machine will operate when current is flowing through plug 116 (i.e., FIG. 1) and will trip the emergency stop to stop the materials testing machine 300 and halt movement of the probe 110 when the contact switch 108 is open and current is not supplied to plug 116 (i.e., FIG. 2).

The coil spring 106 is seated within upper casing 104 and loaded in the compression mode. The lower end of coil spring 106 is engaged to the probe body 138 of lower probe 110. Lower probe 110 terminates in lower probe tip 112. Load cell coupling 114 extends vertically and integrally from the upper cap 115 of upper casing 104 to the materials testing machine 300. Load cell coupling 300 may further include a disk-shaped stop element 119 which is positioned immediately above the upper cap 115. Lower probe 110 extends through an aperture 123 formed in lower cap 121 of lower casing 102.

In FIG. 1, an electrical contact switch 108 is formed between switch component 109 and first and second semi-cylindrical electrical contacts 111, 113, thereby completing the circuit to plug 116 and allowing current to flow therethrough. However, in FIG. 2, when the switch component 109 is raised, in concert with the compression of coil spring 106 as shown in FIG. 2, the electrical contact switch 108 is opened, this circuit is broken and no current is allowed to flow between the first and second semi-cylindrical electrical contacts 111, 113 and no current flows through plug 116.

As shown in FIG. 1, the coil spring 106 is preloaded to the desired safety load thereby in the probe assembly 100 directly passing the load from the lower probe tip 112 via the load cell coupling 114 to the load cell of materials testing machine 300 for loads under the point where the coil spring 106 additionally compresses. In other words, the force applied at the lower probe tip 112 directly transfers through the preloaded compression spring 106 to the upper cap 115 and load cell coupling 114 and ultimately to the load cell. As shown in FIG. 2, upon deflection of the coil spring 106 in excess of safety preload, the coil spring 106 internally compresses within the upper casing 104 of probe assembly 100 rather than the lower probe tip 112 continuing to displace into the specimen or test surface 200. The compression of the coil spring 106 continues upon additional displacement by the drive system of the materials testing machine 300 until an electrical contact within electrical contact switch 108 is broken. In other words, upon overloading travel, the coil spring 106 compresses causing relative motion within the probe assembly 100 until electrical contact is broken. The stiffness or Hooke's constant of the spring 106 is chosen so that this occurs at the desired force breakpoint or threshold. The electrical contact switch 108 is wired to the emergency stop of the materials testing machine 300 via plug 116 and when it is broken, the emergency stop is tripped and instantly shuts down the materials testing machine 300 preventing any further motion of the probe 110 and damage to the specimen 200. Again, FIG. 1 shows the probe 110 in its normal state applying light loads to the specimen 200. FIG. 2 shows the probe coupling and the coil spring 106 undergoing compression beyond the safe preload and displacement limit, thereby breaking the electrical contact of electrical contact switch 108 and tripping the emergency stop via plug 116 to stop the materials testing machine 300 and halt movement of the probe 110.

Figure 4:
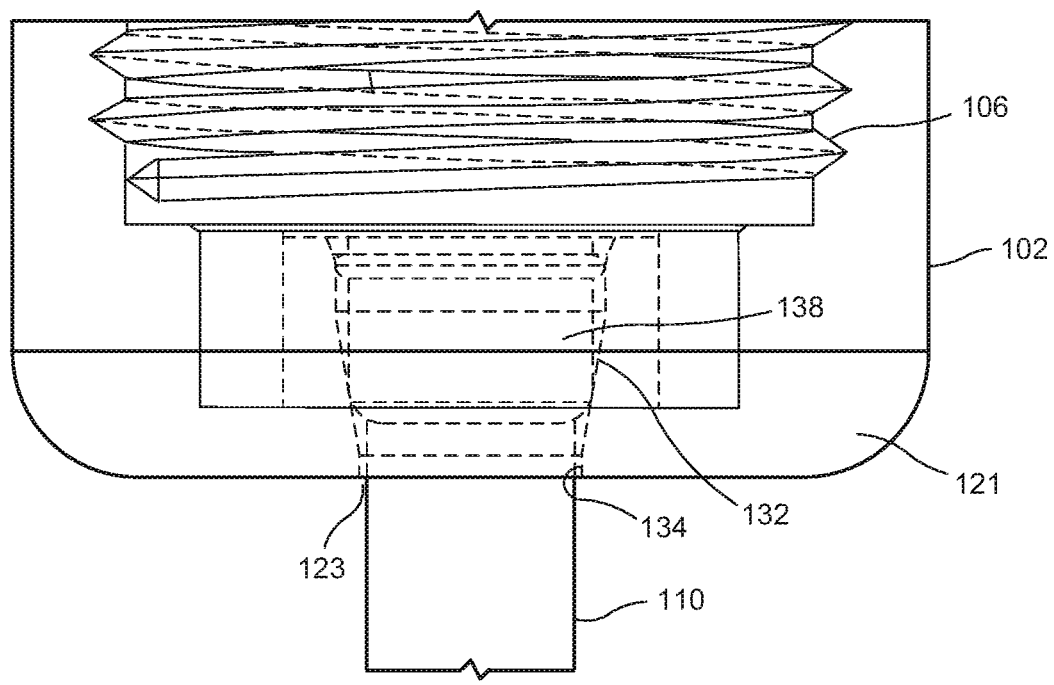
FIG. 4 is a detailed view of the first embodiment of the probe assembly of the present disclosure.
Figure 5:
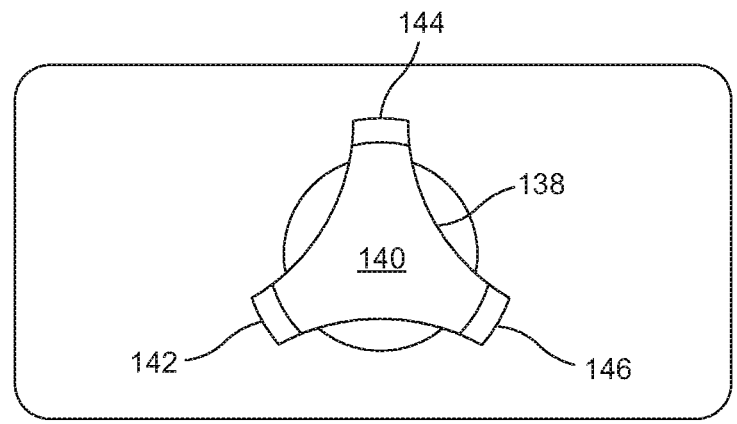
FIG. 5 is an upper plan view a portion of the probe assembly of FIG. 4.
Figure 6:
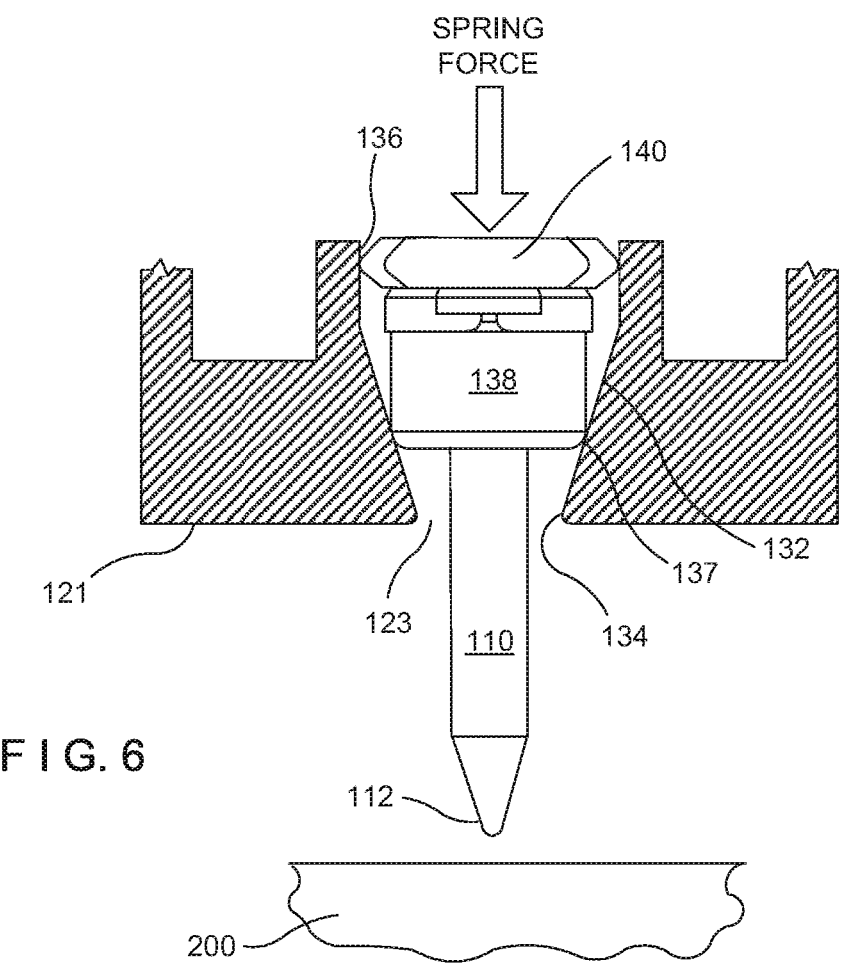
FIG. 6 is a cut-away view of a portion of the probe assembly of FIGS. 5 and 5.

FIGS. 4 and 6 show the detail of aperture 123 in lower cap 121 of lower casing 102 as well as that of lower probe 110. Aperture 123 includes lower conical shaped section 132 with a lower opening 134 of reduced diameter, and an upper cylindrically shaped bore 136. Lower probe 110 includes lower tip 112 which, as previously described, contacts specimen 200. Lower probe 110 further includes lower probe body 138 of increased diameter above the lower tip 112 and contact pad assembly 140 above the lower probe body 138. In this embodiment, the lower end of spring 106 may engage the lower probe 110 by wrapping around lower probe body 138. As shown in FIG. 5, the contact pad assembly 140 is a tri-lobular protrusion with first, second and third radially extending contact pads 142, 144, 146. The radiused bottom edge 137 of lower probe body 138 contacts the lower conical shaped section 132 of aperture 123 in an essentially circular ring of contact. This ring of contact, along with the nesting force of coil spring 106 resolves the three linear degrees of freedom (side-to-side, front-to-back and up-and-down) of the lower probe body 138. Similarly, the configuration of the contact pad assembly 140, with the first, second and third radially extending contact pads 142, 144, 146 contacting the upper cylindrically shaped portion 136 of aperture 123, resolves two annular tipping motions (front-to-back and side-to-side) by a disk in a bore connection. The tri-lobular protrusions of the contact pad assembly 140 fit into the upper cylindrically shaped bore 136 of aperture 123 with a line-to-line fit. First, second and third radially extending contact pads 142, 144, 146 are used thereby allowing slight wear of the pads if the parts fit with interference. Contact pads 142, 144, 146 may be made of plastic to allow for such wear. The rotational degree of freedom is not address as lower probe 110 is rotationally symmetric, so rotation is not expected to impact the mechanics of the probe assembly 100.

Figures 7, 8:
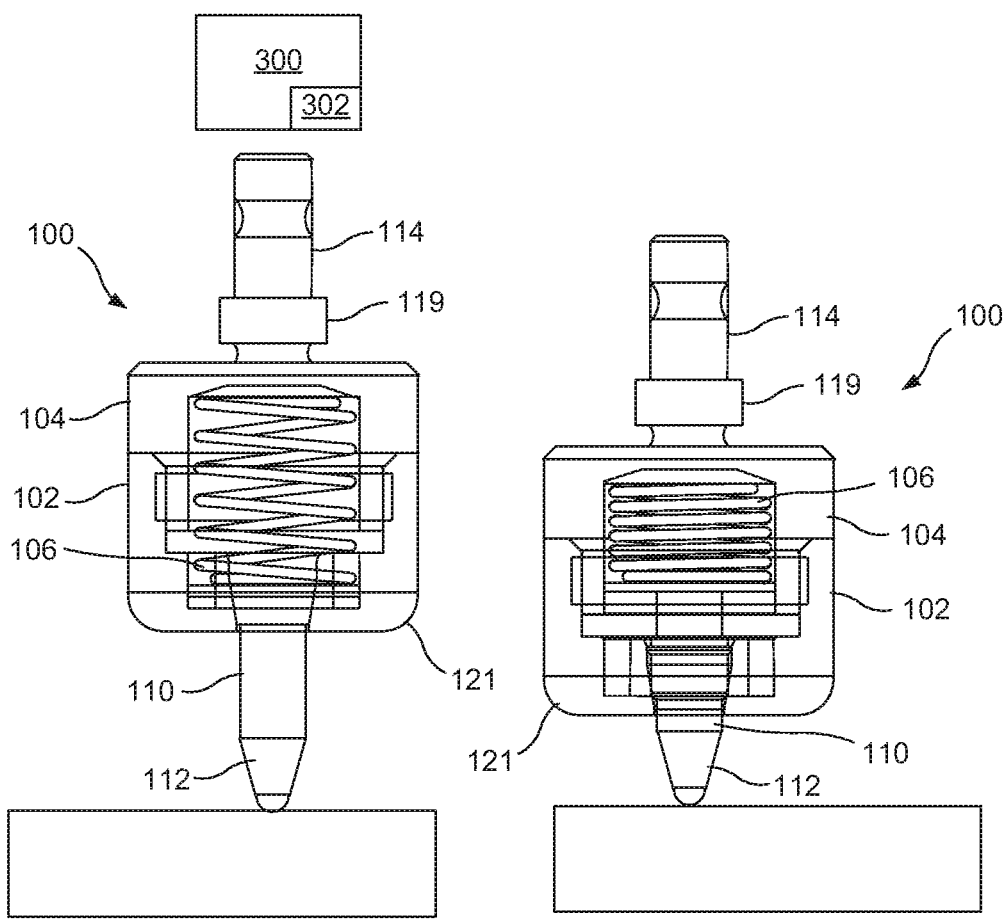
FIG. 7 is a cross-sectional view of a second embodiment of the probe assembly of the present disclosure, in a normal state.
FIG. 8 is a cross-sectional view of a second embodiment of the probe assembly of the present disclosure, in a safety or compressed state.

FIGS. 7 and 8 disclose a second embodiment of the probe assembly 100 of the present disclosure. This embodiment is similar to the first embodiment of FIGS. 1-3. However, the switching function is removed from the interior of the probe assembly so that lateral aperture 107, electrical contact switch 108, switch component 109, first and second semi-cylindrical electrical contacts 111, 113 and plug 116 are omitted. Rather, the associated testing machine 300 (particularly travel detector module 302) detects the drive system's excessive travel past a pre-determined threshold (as evidenced by the position of the load cell coupling 114)

allowed by the deflection of the coil spring 106 as shown in FIG. 8, and switches off the drive system of the associated testing machine 300.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A probe assembly for materials testing, comprising;
   a probe arranged and configured for contact with a materials testing sample, the probe further including a component of a switch mechanism wherein, in a first position of the probe, the switch mechanism is closed and, in a second position of the probe, the switch mechanism is open;
   a load cell coupling arranged and configured to be driven by a materials testing machine;
   a spring placed between the probe and the load cell coupling;
   a first cylindrical wall portion surrounding at least a portion of the probe, the first cylindrical wall portion including a first cap, the first cap including an aperture through which the probe extends;
   a second cylindrical wall portion surrounding at least a portion of the spring, the second cylindrical wall portion including a second cap from which the load cell coupling extends;
   the spring, in response to forces below a pre-selected threshold, transfers force between the probe and the load cell coupling and maintains the probe in the first position so that the switch mechanism is in a closed configuration, and, in response to force above a pre-selected threshold, compresses and moves the probe to the second position so that the switch mechanism is open.

2. The probe assembly of claim 1 wherein the spring is a coil spring loaded in a compression state.

3. The probe assembly of claim 1 wherein the second a first end of the spring engages the probe and a second end of the spring is nested within the second cap.

4. The probe assembly of claim 3 wherein the switch assembly includes a plug extending through the first cylindrical wall portion.

5. The probe assembly of claim 3 wherein the switch assembly is arranged and constructed to be operatively connected to a materials testing machine.

6. The probe assembly of claim 3 wherein the switch assembly is arranged and constructed to be electrically wired to a stop mechanism of a materials testing machine driving the load cell coupling.

7. The probe assembly of claim 3 wherein the first cylindrical wall portion is separable from the second cylindrical wall portion.

8. The probe assembly of claim 7 wherein the first cylindrical wall portion includes an inner cylindrical wall portion and wherein the second cylindrical wall portion fits concentrically over the inner cylindrical wall portion.

9. The probe assembly of claim 3 wherein the probe includes a tip for contacting a materials testing sample.

10. The probe assembly of claim 3 wherein the first cylindrical wall portion and the second cylindrical wall portion have a common longitudinal axis.

11. The probe assembly of claim 1 wherein the load cell coupling includes a mechanical stop element to limit travel of the load cell coupling into the second cylindrical wall portion.

12. A probe assembly for materials testing, comprising:
    a probe arranged and configured for contact with a materials testing sample, a portion of the probe being surrounded by a first wall portion which includes a first cap with an aperture through which the probe extends;
    a load cell coupling arranged and configured to be driven by a materials testing machine, the load cell coupling extending from a second cap of a second wall portion;
    a spring placed between the probe and the load cell coupling;
    the spring, in response to forces below a pre-selected threshold, transfers force between the probe and load cell coupling and maintains the probe in the first position and, in response to force above a pre-selected threshold, compresses and moves the probe to the second position;
    the second position causing the probe to travel past a pre-determined threshold which is detected by the materials testing machine, and operation of the materials testing machine is terminated by detection of travel of the probe past the pre-determined threshold.

13. The probe assembly of claim 12 wherein the spring is a coil spring loaded in a compression state.

14. The probe assembly of claim 12 wherein a first end of the coil spring engages the probe and a second end of the spring is nested within the second cap.

* * * * *